United States Patent [19]

Kleiner

[11] Patent Number: 5,481,017

[45] Date of Patent: Jan. 2, 1996

[54] METHOD FOR PREPARING 6H-DIBENZO[C,E][1,2]OXAPHOSPHORIN-6-ONE

[75] Inventor: Hans-Jerg Kleiner, Frankfurt am Main, Germany

[73] Assignee: Hoechst Aktiengesellschaft, Frankfurt am Main, Germany

[21] Appl. No.: 268,829

[22] Filed: Jun. 30, 1994

[30] Foreign Application Priority Data

Jul. 3, 1993 [DE] Germany .......................... 43 22 168.8

[51] Int. Cl.⁶ .................................................. C07F 9/6574
[52] U.S. Cl. ............................................... 558/82; 558/122
[58] Field of Search ........................................ 558/122, 82

[56] References Cited

U.S. PATENT DOCUMENTS

4,086,206  4/1978  Saito et al. .

FOREIGN PATENT DOCUMENTS

2034887    1/1972  Germany .
2730371    1/1978  Germany .
47-016436  9/1972  Japan .

OTHER PUBLICATIONS

Journal of General Chemistry of the USSR, "Organophosphorus Heterocyclic Compounds" vol. 42, pp. 87–90, Jan. 1972.
Chemical Abstracts, vol. 103, No. 11, Sep. 16, 1985, abstract No. 88080e.
Chemical Abstracts, vol. 77, No. 23, Dec. 4, 1972, abstract No. 152357z.

*Primary Examiner*—Robert W. Ramsuer
*Assistant Examiner*—Michael G. Ambrose
*Attorney, Agent, or Firm*—Connolly and Hutz

[57] ABSTRACT

Process for the preparation of 6H-dibenzo [c,e][1,2]oxaphosphorin-6-one of the formula

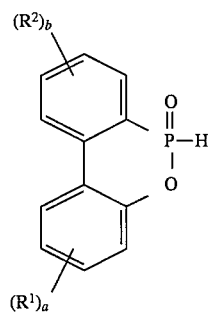

in which $R^1$ and $R^2$ are identical or different and are halogen or an alkyl or alkoxy group having from 1 to 6 carbon atoms and a and b are identical or different and are 0, 1, 2 or 3, which involves reacting a 6-chloro-(6H)-dibenzo[c,e][1,2] oxaphosphorin of the formula

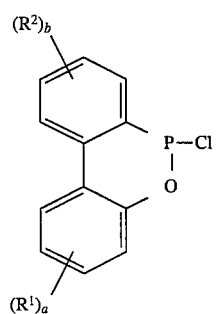

in which $R^1$, $R^2$, a and b are as defined above, with water in a molar ratio of 1:1 at from 50° to 250° C., in the presence if desired of a solvent, and separating off gaseous hydrogen chloride at the rate at which it is formed.

10 Claims, No Drawings

METHOD FOR PREPARING 6H-DIBENZO-[C,E] [1,2] OXAPHOSPHORIN-6-ONE

DESCRIPTION

Process for the preparation of 6H-dibenzo[c,e][1,2]oxaphosphorin-6-one

The present invention relates to an improved process for the preparation of 6H-dibenzo[c,e][1,2]oxaphosphorin-6-one of the formula (I)

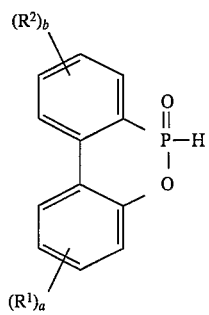

6H-Dibenzo[c,e][1,2]oxaphosphorin-6-one, like its ring-substituted derivatives, is an important intermediate in the production of flame retardants (see also DE-C 26 46 218, DE-C 27 30 371 and DE-C 29 20 718). The above-mentioned oxaphosphorin-6-ones can also be used as promoters in polymerization processes (see EP-A-0 454 462).

It is known to prepare 6H-dibenzo [c,e][1,2]oxaphosphorin-6-one starting from 6-chloro-(6H)-dibenzo[c,e][1,2]oxaphosphorin. The 6-chloro-(6H)-dibenzo [c,e][1,2]oxaphosphorins (II) required for this purpose can be obtained reacting corresponding o-phenylphenols with $PCl_3$ (see DE-C 27 30 371 and DE-C 26 34 887).

In accordance with Example 1 of DE-C 27 30 371 6-chloro-(6H)-dibenzo[c,e][1,2]oxaphosphorin is hydrolyzed excess water, employing an excess of water of more than 100% in relation to the stoichiometry of the reaction. This inevitably leads to waste waters which are polluted to a high degree with hydrochloric acid. Such waste waters not only are undesirable because of their corrosive properties but also give rise to difficulties at the disposal stage.

The hydrolysis of 6-chloro-(6H)-dibenzo[c,e][1,2]oxaphosphorin with water, however, does not lead exclusively to the formation of 6H-dibenzo[c,e][1,2]oxaphosphorin-6-one. To avoid the difficulties which this entails, JP-47-16436 recommends—as explained in more detail below—that the hydrolysis be carried out with an excess of water and that subsequently water be eliminated from the reaction product obtained in the hydrolysis.

The hydrolysis of 6-chloro-(6H)-dibenzo [c,e][1,2]oxaphosphorin proceeds as follows (see also equations (4) and (5) of JP-47-16436):

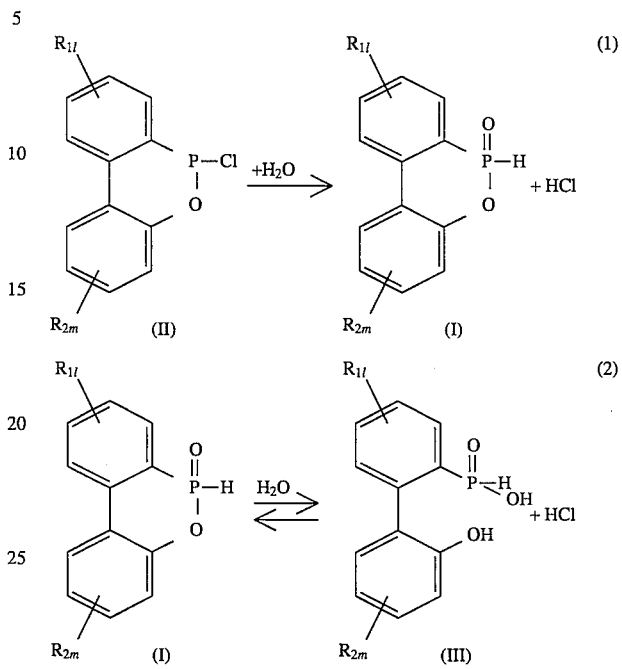

($R_1$ and $R_2$ are for example halogen or an allyl or alkyl group and l and m are an integer between 0 and 4.)

The initial product which forms from the 6-chloro-(6H)dibenzo[c,e][1,2]oxaphosphorin (II) with irreversible elimination of HCl is the corresponding (6H)-dibenzo[c,e][1,2]oxaphosphorin-6-one (I) [equation (1)] which, however, quickly reacts further with water to give the corresponding phosphinic acid (III) according to equation (2). For this reason it is very difficult to curtail the hydrolysis at the stage of the (6H)-dibenzo[c,e][1,2]oxaphosphorin-6-one. Consequently the teaching of JP-47-16436 recommends carrying out the hydrolysis with an excess of water and separating off the phosphinic acid (III) which is formed in this hydrolysis, in order to convert this acid, in a separate step with elimination of water, into the corresponding 6H-dibenzo-oxaphosphorin. For this purpose (III) is melted and the water which forms is removed with the application of a vacuum.

The process described in JP-47-16436 not only is extremely complicated and difficult to manage at an industrial level but also leads—as already mentioned in connection with DE-C 27 30 371—inevitably to the production of waste waters containing hydrochloric acid.

There was therefore a need to develop a process which avoids the abovementioned disadvantages, can be carried out on an industrial level without great complexity and which, in addition, renders the desired products accessible both in high yield and in high purity.

This object is surprisingly achieved by a process for the preparation of (6H)-dibenzo[c,e][1,2]oxaphosphorin-6-one of the formula

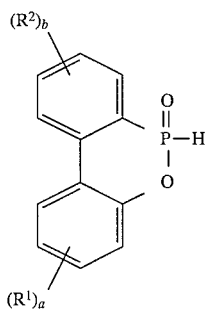

in which $R^1$ and $R^2$ are identical or different and are halogen or an alkyl or alkoxy group having from 1 to 6 carbon atoms and a and b are identical or different and are 0, 1, 2 or 3. It comprises reacting a 6-chloro-(6H)dibenzo[c,e][1,2]oxaphosphorin of the formula

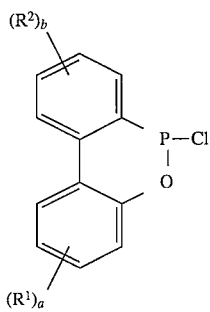

in which $R^1$, $R^2$, a and b are as defined above, with water in a molar ratio of 1:1 at from 50° to 250° C., in the presence if desired of a solvent, and separating off gaseous hydrogen chloride at the rate at which it is formed.

Halogen comprehends chlorine or bromine. Examples of alkyl groups are methyl, ethyl, n-propyl, isopropyl, n-butyl, isobutyl, n-pentyl, isopentyl, 3-methylbutyl, n-hexyl and isohexyl radicals.

Examples of alkoxy groups are methoxy, ethoxy, propoxy, butoxy, pentyloxy and hexyloxy radicals.

$R^1$ and $R^2$ are in particular chlorine, an alkyl group having from 1 to 4 carbon atoms or an alkoxy group having from 1 to 4 carbon atoms.

a and b are independently of one another an integer of between 0 and 3, in particular 0, 1 or 2 and preferably 0 or 1.

The process is well suited to the preparation of compounds of the formula (I) in which a and b are identical and are each 0 or 1, in particular 0.

The reaction proceeds even at relatively low temperatures, but it is recommended to work at elevated temperatures in order not to be subject to comparatively long reaction times. In many cases it is sufficient to carry out the reaction at from 70° to 200° C., in particular from 100° to 180° C.

The reaction can be allowed to proceed in the absence of a solvent. In a number of cases, however, it may also be sensible to employ a suitable solvent in the reaction. Examples of suitable solvents are aromatic compounds, especially aromatic hydrocarbons.

Well-suited solvents are toluene, o-xylene, m-xylene, p-xylene, ethylbenzene, chlorobenzene, dichlorobenzene or mixtures of these solvents, especially toluene, o-xylene, m-xylene, p-xylene, chlorobenzene or mixtures thereof.

To carry out the process according to the invention the feed material (II) and water are mixed in a molar ratio of 1:1 with intensive stirring at the temperature indicated. A particularly favorable embodiment of the process according to the invention comprises the initial introduction of the 6-chloro-(6H)-dibenzo[c,e][1,2]oxaphosphorin (II) and the addition of the water (in a molar ratio of 1:1) with thorough mixing at the reaction temperature indicated, in the presence if desired of a solvent. For carrying out the process it is sufficient to add water only in the stoichiometric quantity. Using water in a molar ratio of 6-chloro-(6H)-dibenzo [c,e] [1,2] oxaphosphorin:water which exceeds 1:1 is, surprisingly, not necessary.

In the course of the reaction gaseous hydrogen chloride is evolved, which is led off at the rate at which it forms and, if desired, can be processed to give a concentrated hydrochloric acid or is absorbed using an aqueous alkali or an aqueous amine solution. The removal of the hydrogen chloride gas can be very effectively assisted simply by passing in an inert gas, for example nitrogen. It is also possible to dispense with passing in an inert gas. In this case, the expulsion of the hydrogen chloride may if desired be promoted by applying a vacuum. However, it is also possible to dispense with the application of a vacuum and to remove the gaseous hydrogen chloride at atmospheric pressure.

It is surprising that under the reaction conditions virtually quantitative removal of the hydrogen chloride can be achieved, and that the end product contains only small amounts of hydrogen chloride.

A further feature to be regarded as surprising is that, at the reaction temperatures indicated, no decomposition occurs and, in addition, the desired end product of the formula (I) is obtained as the sole reaction product, despite JP-47-16436 teaching that the formation of the corresponding phosphonic acid (III), in addition to unreacted feedstock (I), would have been expected.

The crude product obtained contains <0.1% of hydrogen chloride and is already pure enough (degree of purity at least 95%) in numerous cases to undergo further processing directly, that is without additional purification.

The process according to the invention can be implemented either continuously or batchwise.

The examples below illustrate the process without limiting it.

EXPERIMENTAL SECTION

Example 1 (With Solvent)

2800 g (11.94 mol) of 6-chloro-(6H)-dibenzo[c,e][1,2] oxaphosphorin are initially introduced with 2200 ml of toluene and are heated to 70° C. with intensive stirring.

215 g (11.94 mol) of water are subsequently added over the course of about 6 hours, during which some of the hydrogen chloride gas produced departs. The temperature is subsequently raised in steps until reflux is achieved and is maintained until no further hydrogen chloride is evolved (a period of from 9 to 10 hours). 3500 ml of toluene are added to the reaction mixture at 100° C., the reaction mixture is cooled, and the solid product which results is filtered off with suction and washed with 1000 ml of toluene.

After drying has been carried out, 2380 g of 6H-dibenzo[c,e][1,2]-oxaphosphorin-6-one (melting point: 117° to 120° C.) are obtained. A further 140 g of the desired product (melting point: 117° to 119° C.) are recovered from the filtrate. The overall yield is 2520 g of 6H-dibenzo[c,e][1,2]-oxaphosphorin-6-one, corresponding to a yield of 98% of theory.

Example 2 (Without Solvent)

77.6 g (0.331 mol) of 6-chloro-(6H)-dibenzo[c,e][1,2] oxaphosphorin are heated to 110° C. 5.96 g (0.331 mol) of water are subsequently added over the course of 30 minutes with vigorous stirring, during which some of the hydrogen chloride gas produced departs. The temperature is subsequently raised in steps to 180° C. and is maintained until no further hydrogen chloride is evolved (a period of approximately 2 hours). The reaction product is subsequently cooled, solidifies, and is comminuted. 71.5 g of 6H-dibenzo[c,e][1,2]-oxaphosphorin-6-one (melting point: 117° C.) are obtained, corresponding to a yield of 100 % of theory. In accordance with $^{31}$P NMR spectroscopy the purity is 99%, and the content of hydrogen chloride is 0.08%.

I claim:

1. A process for the preparation of 6H-dibenzo[c,e] [1,2]-oxaphosphorin-6-one of the formula in which $R^1$ and $R^2$ are identical or different and are halogen or an alkyl or alkoxy group having from 1 to 6 carbon atoms and a and b are identical or different and are 0, 1, 2 or 3, which comprises reacting a 6-chloro-(6H)-dibenzo[c,e] [1,2] oxaphosphorin of the formula in which $R^1$, $R^2$, a and b are as defined above, with water in a molar ratio of 1:1 at from 50° to 250° C., in the presence if desired of a solvent, and separating off gaseous hydrogen chloride at the rate at which it is formed.

2. The process as claimed in claim 1, wherein $R^1$ and $R^2$ are chlorine or an alkyl or alkoxy group having from 1 to 4 carbon atoms.

3. The process as claimed in claim 1, wherein a and b are 0, 1 or 2.

4. The process as claimed in claim 1, wherein a and b are identical and are 0 or 1.

5. The process as claimed in claim 1, wherein the reaction is carried out at from 70° to 200° C.

6. The process as claimed in claim 1, wherein the reaction is carried out at from 100° to 180° C.

7. The process as claimed in claim 1, wherein an aromatic compound is employed as solvent.

8. The process as claimed in claim 1, wherein toluene, o-xylene, m-xylene, p-xylene, chlorobenzene, dichlorobenzene or a mixture thereof is employed as solvent.

9. The process as claimed in claim 1, wherein a and b are 0 or 1.

10. The process as claimed in claim 1, wherein a and b are identical and are 0.

* * * * *